United States Patent [19]

Schoendorfer et al.

[11] 4,223,411
[45] Sep. 23, 1980

[54] INTERNAL LARYNGEAL PROSTHESIS

[75] Inventors: Donald W. Schoendorfer, Brookline; Stephen A. Raymond, Carlisle, both of Mass.

[73] Assignee: Massachusetts Institute of Technology, Cambridge, Mass.

[21] Appl. No.: 931,494

[22] Filed: Aug. 7, 1978

[51] Int. Cl.² .............................................. A61F 1/20
[52] U.S. Cl. ..................................... 3/1.3; 128/207.16
[58] Field of Search ............................ 3/1.3; 128/351; 179/1 AL

[56] References Cited

U.S. PATENT DOCUMENTS

| 3,747,127 | 7/1973 | Taub ......................................... 3/1.3 |
| 4,044,402 | 8/1977 | Edwards ................................... 3/1.3 |

OTHER PUBLICATIONS

The Artificial Larynx (Book) by Yvan Lebrun, 1973, pp. 53–56.

*Primary Examiner*—Ronald L. Frinks
*Attorney, Agent, or Firm*—Arthur A. Smith, Jr.; Martin M. Santa

[57] ABSTRACT

An internally worn laryngeal prosthesis for laryngectomized patients is described. The prosthesis is worn internally at the end of a surgically constructed fistula leading to the base of the patient's vocal tract. Exhaled air powers a miniature vibratory mechanism whose output enters the vocal tract directly and supplies both a voiced and a voiceless sound source. A tube connects the other end of the prosthesis to the tracheostoma from which air from the lungs powers the prosthesis. The tube contains a valve which may be manually or automatically controlled to allow either speech or quiet breathing.

9 Claims, 12 Drawing Figures

INTERNAL LARYNGEAL PROSTHESIS

The Government has rights in this invention pursuant to Grant Number NIH-5-TO1-GMO2136-03 from the National Institute of Health.

BACKGROUND OF THE INVENTION

The prior art of speech rehabilitation available to the laryngectomee includes esophageal, electronic, and fluid mechanical techniques. Esophageal speech is difficult and time-consuming to learn. Thirty to fifty percent of all who try to learn fail. The esophageal speaker's voice has often been rated as unsatisfactory. Electronic prostheses are fairly easy to learn to control, but produce unnatural, mechanical speech. Fluidmechanical prostheses, which use the patient's lungs as an air flow source, currently have two important deficiencies: (1) they introduce their acoustic source into the mouth or nose, thus insuring in principle an unnatural voice; (2) the vibrating elements do not supply the vocal tract with a voiced source whose spectral energy is suitable for natural-sounding speech.

One prior art technique uses a fluid-mechanical prosthesis which overcomes the first deficiency. This reed-fistula speech rehabilitation technique developed by S. Taub and advanced by D. Shedd, introduces the acoustic output of a fluid-mechanical prosthesis indirectly into the lower regions of the vocal tract near the area of the excised larynx. This is possible only after surgical construction of a skin-lined tube or skin fistula 1, between the region of the lower neck and the vocal tract as depicted in FIGS. 1A and 1B. The patient wears the prosthesis 2 externally. The inlet tube 3 fits into the tracheostoma 4. The outlet tube, or fistula tube 5, inserts into the skin fistula 1. During normal breathing, the valve 6 is open, and the patient inhales and exhales through the breathport 7. The valve 6 is closed during speech. If the patient exhales below a preset air flow level, air passes through the prosthesis 2 up the fistula tube 5 and into the vocal tract 8. This air flow can be used to create voiceless phonemes. If the patient exhales more vigorously, a mechanical vibratory mechanism 9 inside the prosthesis 2 is set into oscillation, producing pulsations on the through flow. This pulsatile acoustic source can be used to create voiced phonemes, but the quality of speech suffers since the oscillations must pass through the fistula tube 5 before entering the vocal tract. Also much of the sound generated in the external prosthesis is transmitted directly through the air from the vibratory mechanism 9 without passing through the vocal tract.

It is therefore the primary object of this invention to provide a reed fistula prosthesis device which simulates the natural larynx.

It is a further object that the prosthesis should provide normal voice intensity at normal speaking pressures and air flows. Normal ranges are between 4 and 20 cm H$_2$O for pressure and between 110 and 300 cc per sec. for air flow.

It is a further object of the prosthesis to minimize noise radiated directly from the vibratory mechanism.

It is a further object that the prosthesis should have a fundamental frequency agreeable for a male (about 131 Hz) or a female (about 262 Hz). It should also have the feature of frequency modulation for pitch inflection.

It is a further object that the prosthesis supply the vocal tract with an acoustic signal whose energy spectrum is appropriate for normal sounding speech.

It is a further object of the prosthesis to provide a device wherein the quality of the voice, the convenience of the apparatus, the ease of learning to use it and the ease of use, and aesthetics of appearance should sufficiently appeal to the patient that he/she feels pleased with the return of speech.

It is a feature of this invention that the vibratory mechanism is located within the neck in proximity to the vocal tract to allow the vocal tract to be active in forming sounds.

It is a further feature of this invention that it is inexpensive and easy to make and maintain, and that the vibratory mechanism may be replaced when its performance has become degraded through use.

It is a further feature that the size of the device is small to minimize cosmetic distraction.

It is a further feature that the device provides an acoustic source for both voiced and voiceless sounds.

SUMMARY OF THE INVENTION

A laryngeal prosthesis capable of being worn mostly inside a surgically constructed fistula is described. The vibratory mechanism is connected via a tube to a tracheostoma connector. The vibratory mechanism is located within the fistula at the fistula end nearest the base of the vocal tract and includes a vibratory portion to mimic vocal chord behavior that does not provide a valving action. The tube connecting the vibratory mechanism with the tracheostoma connector is as short as possible to minimize resonances within it. The tracheostoma connector is provided with a port so that breathing can bypass the vibratory mechanism when speech is not desired. The port may be opened or blocked manually or by a valve controlled by lung air pressure. A saliva valve is provided at the distal end of the vibratory mechanism to block access except when air is being expelled from the lungs for actuation of the vibratory mechanism. Several forms of vibratory mechanisms small enough to fit within the fistula are described.

DESCRIPTION OF THE DRAWINGS

Other advantages, features, and objects of this invention will appear from the following description taken together with the drawings in which.

DETAILED DESCRIPTION OF INVENTION

A laryngectomy leaves the lungs and most of the vocal tract undisturbed. The patient retains his former speech power supply (the lungs) and tunable acoustic resonator (the vocal tract). However, his power supply is not connected to his resonator, and he has lost his periodic acoustic source generator (the larynx). He could produce voiceless phonemes if an air supply could be made to enter his vocal tract where his excised larynx had been located. Voice phonemes could be made if an artificial periodic acoustic source was directed to enter his vocal tract in this same location. The correct location of entry is important. The vocal tract filter function depends on the location of the excitation source. Prior art prostheses that introduce the acoustic source into the mouth or nose change the relative amplitude of the vocal tract formants. It is remotely possible that the patient could learn to compensate for this distortion by reshaping his vocal tract. However, considering the already difficult adjustment during postoperative recovery, such a requirement for additional training should become a part of the design only as a last alternative.

The only practical means of avoiding the acoustic distortion caused by the downstream tube is decreasing its length. For downstream tubes less than 2 cm long, the first quarter-wave resonance occurs above 400 Hz, low enough not to interfere with voiced formants. Such a constraint on the downstream tube length requires that the prosthesis be worn internally, within 2 cm of the end of the skin fistula. An added advantage derived from wearing the prosthesis internally is that the tissues of the neck would dampen the sound radiated from its walls, as they do for the normal larynx.

Figure 2A:
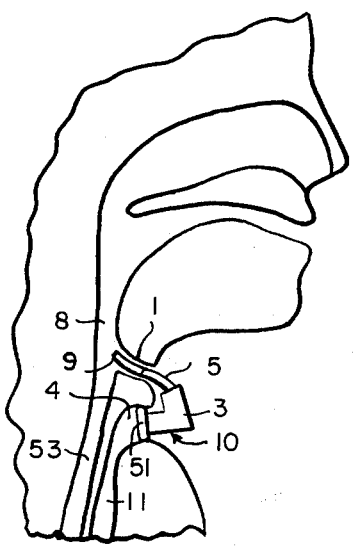
FIGS. 2A and 2B are side and front views of the internal laryngeal prosthesis of this invention.
Figure 2B:
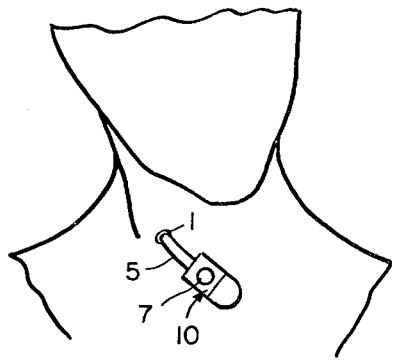

Surgical constraints prohibit significant enlargement of the skin fistula. Therefore a new system was required, small enough to be held in the relatively small cross-sectional area of the skin fistula, approximately 0.4 in. inner diameter (9.5 mm). Over twenty alternative vibration mechanisms were experimented with; two different approaches were successfully miniaturized. FIG. 2 shows how a reed-fistula patient would wear such a prosthesis 10 of this invention where the vibratory mechanism 9 is located adjacent to the vocal tract 8 and connects to the trachea 11 by the fistula tube 5 to the tracheostoma connector 3 which has a catch ring 51 and a breath port 7. The vibratory mechanism 9 and a portion of the tube 5 are inserted into the skin fistula 1 until the end of the vibrator 9 is near the vocal chord region 8 opening connecting with the esophagus 53. The catch ring 51 is inserted into the tracheostoma 4 which connects to the trachea 11.

Figure 3:
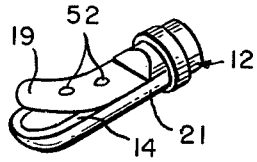
FIG. 3 is an isometric view of a reed type vibratory mechanism of this invention.

FIG. 3 shows a schematic diagram of one of the successful miniature vibratory mechanisms, the duckcall reed mechanism 12. At a preset level of inlet air flow, the reed 19 is pulled against the striker base 14 and interrupts the flow. The elastic forces of the reed return the reed to its initial open position and the cycle is repeated. Miniaturization of the classic duck-call became a major challenge. The difficulty was in providing a mechanism with a low enough fundamental frequency for natural sounding speech. This implied preserving the ratio of the distributed mass of the reed to its nonlinear spring constant. A thin strip of Mylar approximately 3 cm long, and 5 mm thick (other stiff plastics were found to work) was found to vibrate at speech frequencies. The material also developed desired pitch variations with variations in driving pressure (providing a means of voice inflection). The plastic strip could be prebent to adjust its rest position, starting pressure, and force-displacement relationship. Distributed masses 52 (Dow Corning RTV 732) were fixed at experimentally determined locations to tune the reed and control the pitch driving pressure relationship. The type of material used for the reed, it size, shape, and location of distributed masses were used as variables to create a model that would perform favorably at physiological pressures and air flows. The degree of prebending in the reed and the profile of the striker base were used as variables to control starting air flow level and spectral components.

Figure 1A:
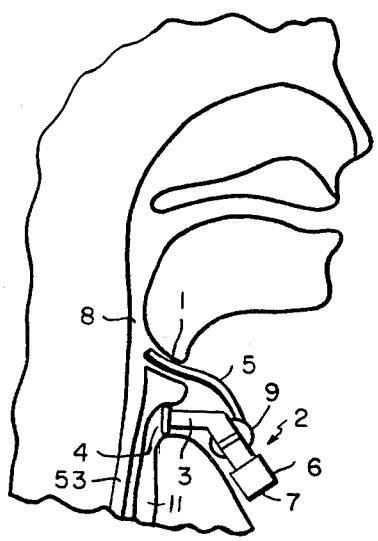
FIGS. 1A and 1B are side and front views of a prior art external laryngeal prosthesis.
Figure 1B:
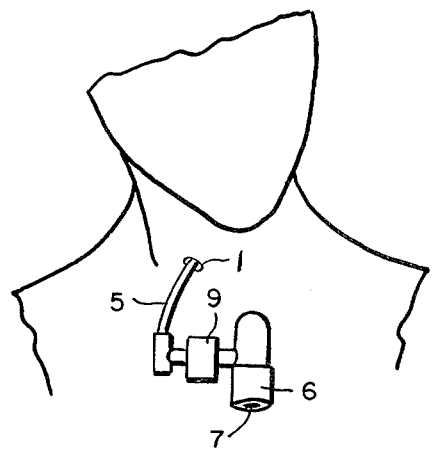
Figure 4:
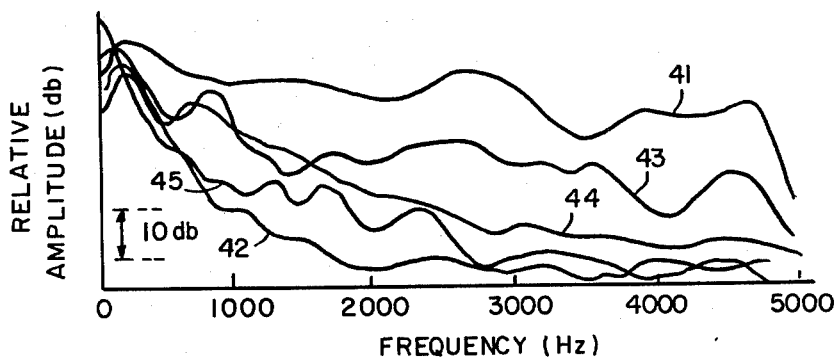
FIG. 4 shows the output spectra for different vibratory mechanisms and a normal vocal chord spectrum.

The vibrator 12 design of FIG. 3 with distributed masses 52 was found to generate an abundance of acoustic energy above 500 Hz relative to the normal vocal chord spectrum as in curve 41 of FIG. 4. The spectrum of the prior art reed fistula prosthesis of FIG. 1 is shown for comparison as curve 42. Also for comparison, curve 45 shows the normal vocal chord spectrum.

Figure 5:
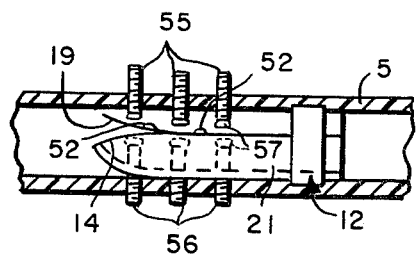
FIG. 5 is a cross-sectional view of a reed mechanism.

It was found that the spectrum of the initial (undamped) model had many formats, as can be seen in curve 41. Experiments with different reed materials (brass, steel, plastic, Myler) showed that 0.005" thick Mylar had the smoothest spectrum. The design of FIG. 3 was modified as shown in FIG. 5 with six adjustable set screws 55, 56 with soft silastic ends 57 (Dow Corning RTV 732) to help shape the output spectrum. The set screws went through tube 5 and were positioned over the antinodes of the second and third modes of the vibratory reed, which were located by stroboscopic observation. Significant improvements in the output spectrum as indicated by curve 43 of FIG. 4 were made by optimally adjusting the set screws to constrain the excursions of the reed 19. (For description of technique used for gathering these spectra refer to "Design, Construction, and Evaluation of a Prosthetic Vocal System", Schoendorfer, PhD Thesis, Massachusetts Institute of Technology, 1977).

Figures 6, 7:
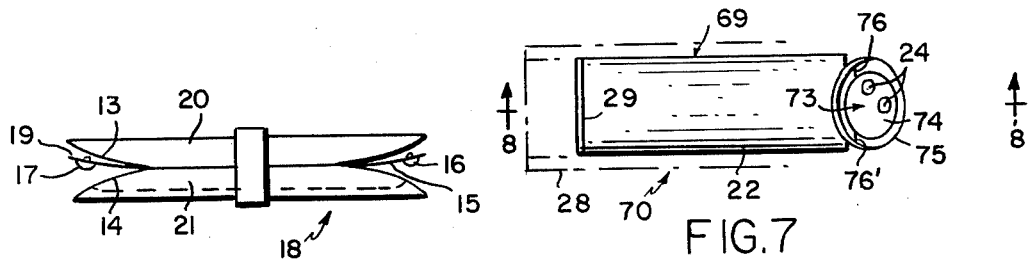
FIG. 6 is the side view of a double reed vibratory mechanism.
FIG. 7 is a top view of the flap valve type vibratory mechanism of this invention.

The spectrum (curve 43) of the optimally damped duckcall reed 12 is much closer to the normal voice chord spectrum. Unfortunately, the sound pressure level (SPL) dropped from 132 db for the undamped case to 128 db. The upper damper screws 55 were then replaced by an upper striker plate 20 of Teflon as shown in FIG. 6 whose profile 13 approximated the positions of the set screws 55. Similarly, the profile 14 of the lower hollow striker plate 21 approximates the positions of the lower set screws 56. The differences in the spectra of the reed with the adjustable dampers and the reed with the shaped striker plates were negligible. Although Teflon was used for the striker plates, other materials would be suitable.

A closer approximation of the normal vocal chord spectrum was made with the addition of a downstream reed 15 as shown in FIG. 6. Tiny, Silastic masses 16, 17 positioned on the reeds 15, 19, respectively, provided a means of matching the resonant features of the downstream reed 15 with the upstream reed 19. The double duck-call reed system 18 of FIG. 6 creates an acoustic output whose spectrum copies the normal vocal chord spectrum closely, as shown in FIG. 4, curve 44. The SPL dropped from 132 db to 123 db at 8 cm $H_2O$ during pressure as a consequence of this spectral tuning. (Normal vocal chords created a relative SPL of 129 db at conversational level).

Figure 8:
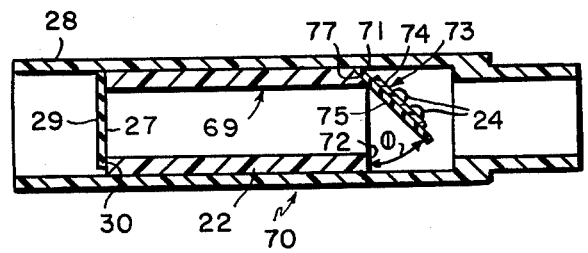
FIG. 8 is a cross-sectional view of the mechanism of FIG. 7.

The second vibratory mechanism, the flap-valve reed mechanism 70, is shown in FIGS. 7 and 8. The spring force in the flap-valve 73 is produced at the bond area 71 by bending of the flap-valve 73, and the surgical tubing striker 22 end 72. This is advantageous because it allowed changing masses and spring constants independently. The flap-valve 73 is constructed of a 0.005" thick 0.24 Dia. Mylar disk 74 glued to a slightly larger disk 75 of 0.005" thick dental dam rubber. The striker 22 is made of 5/16" diameter surgical tubing. The edges of the surgical tubing 22 were sanded on a high speed belt sander to permit fabrication of the smooth surfaces on the striker end 72 and the beveled edge 77 where bond area 71 occurs.

The performance of the flap-valve reed 69 could be controlled by changing the angle $\phi$ between the flap valve 73 and the striker end 72; the size and shape of the Mylar disk; the location and size of distributed masses 24 on the flap-valve 73; and the depth of side slits 76 which control the elastic forces on the flap-valve.

Dental dam rubber chosen because of its ability to seal against the surgical tubing. The Mylar disk 74 gives the dental dam rubber structural support. The angle is determined by the beveled edge 77 of the end 72 of the tubing 22. The flap-valve 73 is attached to the beveled edge 76 which causes the flap-valve 73 to assume the angle $\phi$ with respect to the plane of the end 72. The assembly of the flip-valve 73 and the tubing 22 is termed the flap-valve reed 69. As an example, the angle $\phi$ was determined to be $30°\pm5°$ for the desired performance of starting pressure and frequency. Variation of these parameters allowed production of models which could produce a SPL relative of 127 db with 8 cm $H_2O$ driving pressure. Curve 46 of FIG. 9 indicates that the output spectrum of the flap-valve reed mechanism 70 is smooth and similar to normal spectra, curve 45.

The flap valve reeds are very small compared to the other vibratory mechanisms developed. They have an inherent simplicity in construction.

Figure 9:
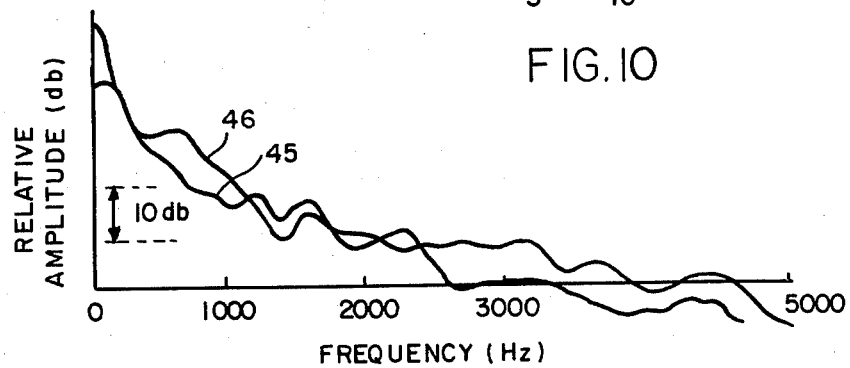
FIG. 9 shows the output spectra of a flap valve type vibratory mechanism and a normal vocal chord spectrum.

FIGS. 4 and 9 indicate that the spectrum are very close to the normal vocal chord spectrum, curve 45, in both the duck call and flap valve reeds. The reeds can be adjusted (by prebending) so that vibration does not occur until the user exhales above a preset pressure. Thus, the user need not be burdened with a manually controlled speech valve or switch. If the user wishes to be silent he exhales below the preset pressure (e.g., 6 cm $H_2O$). If he wants to speak, he raises his exhalation pressure (e.g., 8 cm $H_2O$).

In Vitro Testing. The duck-call reed 12, 18, and flap-valve 69 have very similar performance characteristics. Models can be constructed that have fundamental frequencies between 100 Hz to 400 Hz at 8 cm $H_2O$ driving pressure and 150 $cm^3$/sec air flow. The threshold pressure needed to start vibration and the fundamental frequency are set during construction. The flap-valve reed 69 is pressed into a Teflon housing 28 to form mechanism 70. A diagram of the housing 28 with a flap-valve reed 69 is shown in cross-section in FIG. 8. The housing 28 is reduced in diameter at the flap-valve end 73 in order to allow fistula tube 6 to be connected and to preferably maintain the same overall diameter of the assembly. The same type of housing is used for duck-call reed 12, 18.

The fundamental frequency changes with the driving pressure, enabling the patient to develop pitch inflection. A typical finished model oscillated at fundamentals varying from between 104 Hz to 370 Hz as the driving pressure was increased from 4 to 28 cm $H_2O$ and air flow from 110 to 280 $cm^3$/sec. Varying the driving pressure also varied the output SPL from 120 db to 134 db for the flap-valve reed mechanism 70 and from 110 db to 123 db for the double duck-call reed 18. The intensity changes that occur with normal inflection as the prosthesis is used are not distracting. Subjectively, the inflection was distinctly pleasant, especially if compared to the mechanical deadpan associated with other prostheses.

The transient times needed to develop or diminish a full vibration waveform for both prostheses required 4 pitch periods compared to 5 to 6 pitch periods measured for normal vocal chords. This makes it possible for a patient to be able to develop adjacent voiced-voiceless sounds.

The problem of fluid leakage from the pharynx through the skin fistula 1 in the reed-fistula technique has been a major concern, both because of its cosmetic inconvenience and because it can interfere with the performance of the prosthesis. There are two routes of fluid leakage: (1) inside vibratory mechanism and down the fistula tube 5, and (2) between skin fistula and internally worn prosthesis, exiting onto the patient's neck and chest.

Leakage into the vibratory mechanism 70 is blocked by the saliva valve 29 shown in FIGS. 7, 8. Cyanocrylate glue is used to fix part of the edge of an 8.7-mm diameter disk 27 of 0.005"-thick (0.12 mm) dental dam rubber to the base 30 of tubing 22 to form the valve 29. The valve 29 was designed to operate in the presence of saliva which gave it a perfect seal against the base 30 of the reed tubing 22. Less than 0.5 cm $H_2O$ is needed to open the valve completely. Spectral analysis has indicated that it does not modify the output of the reed. The saliva valve 29 is recessed 6 mm into the Teflon housing 28 to protect it from being fouled by the skin fistula. Clinical testing of the valve has been very satisfying. It prevents leakage completely in short-term tests.

Figure 10:
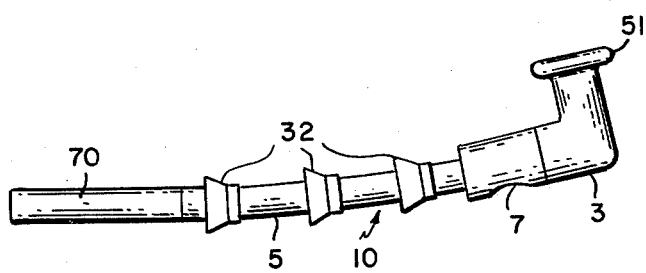
FIG. 10 is a side view of a preferred embodiment of a laryngeal prosthesis of this invention.

A method of preventing leakage between skin fistula 1 and prosthesis 10 is depicted in FIG. 10. Tiny molded latex skirts 32 are attached to the fistula tube 5. The patient folds the skirts back upon themselves as the prosthesis is inserted into his skin fistula. The fistula tube is then withdrawn a few centimeters, causing the skirts to spring open and seal themselves against the walls of the skin fistula. When used in conjunction with the saliva valve, leakage from the pharynx has been essentially prevented in the short-term (<1 day) tests performed thus far.

Conclusion

An internally worn prosthetic system has been shown to overcome two problems which arise with externally worn systems, that of downstream tube resonances and that of interfering acoustic radiaton. The two internally worn systems developed have acoustic outputs with spectral components similar to the normal larynx. They have been designed to supply the patient with sufficient acoustic energy to allow conversation at normal volumes with normal lung pressures, air flows, and fundamental frequencies. They permit pitch inflection by varying driving pressure.

It will also be apparent that the breath port 7 instead of being mannually closed when speech is desired may be automatically closed by a valve (not shown) responsive to lung air pressure slightly less than the valve at which the vibratory mechanism 70 will begin to vibrate.

The valve may assume, for example, the form of a reed which is normally open and which closes in response to the desired lung air pressure.

It is evident that those skilled in the art, once given the benefit of the foregoing disclosure, may make numerous other uses and modifications of, and departures from the inventive concepts. More specifically, the materials specified in the embodiments of the invention, i.e., Teflon, nylon, dental dam rubber, etc., are merely exemplary and other suitable materials will be apparent to those skilled in the art. Consequently, the invention is to be construed as embracing each and every novel combination of features present in, or possessed by, the apparatus and techniques herein disclosed and limited solely by the scope and spirit of the appended claims.

What is claimed is:

1. A laryngeal prosthesis one end of which is adapted to be positioned at the inner end of a surgically constructed fistula leading to the base of the user's vocal tract, the other end of said prosthesis being adapted to be connected to the user's tracheostoma, the prosthesis comprising,
   a vibratory mechanism, adapted to be contained within said fistula near to and at the internal opening of the base of the user's vocal tract, said vibratory mechanism comprising a vibratory portion specifically to mimic vocal chord behavior, said vibrating portion not providing valving action,
   a tube connected at one end to said vibratory mechanism, said tube being adapted to be within said fistula but also extending beyond the external opening of said fistula so that the other end of said tube is outside the fistula,
   a breath port structure having one end connected to the other end of said tube, said breath port structure having another end adapted to be inserted into the tracheostoma, said breath port structure containing a breath hole capable of being closed when air is to be expelled from the lungs through said breath port structure, said tube, and said vibratory mechanism,
   said breath hole when not closed providing an opening adapted to expelling air from the lungs without the air passing through said tube and vibratory mechanism,
   said vibratory mechanism being adapted to being removably inserted into the fistula so that the innermost end of the vibratory mechanism is at the base of the vocal tract.

2. The prosthesis of claim 1 wherein said breath port hole is capable of being manually closed when said vibratory mechanism is desired to be actuated for speech generation.

3. The prosthesis of claim 1 wherein said vibratory mechanism comprises,
   a first cylinder,
   a disk attached to one end of said first cylinder and adapted to close intermittently at a frequency against the one end of said cylinder in response to air pressure against said disk produced by the lung,
   said cylinder being of sufficiently small diameter and length to be capable of insertion into the skin fistula of the user.

4. The vibratory mechanism of claim 3 wherein said one end of said first cylinder has a beveled portion, said disk being attached to said beveled portion to thereby assume a position at an angle with respect to the remainder of said one end, the lung air pressure required to close said disk against said remainder of said end being dependent upon the resistance to bending of the disk and compliance in said beveled portion of said first cylinder to form a flap valve.

5. The vibratory mechanism of claim 4 comprising in addition,
   said first cylinder having a saliva valve attached to its other end, said valve being normally closed and responsive to lung air pressure to open when speech is desired.

6. The vibratory mechanism of claim 5 comprising in addition a housing wherein said first cylinder is rigidly contained within said housing which extends beyond said flap valve and said saliva valve of said first cylinder,
   said housing being smaller in diameter than said skin fistula.

7. The vibratory mechanism of claim 3 wherein said disk has at least one mass attached to the movable portion of said disk to change the vibratory frequency of said disk.

8. The prosthesis of claim 1 wherein said vibratory mechanism comprises,
   a first reed,
   an upper and a lower striker plate against which said reed strikes when vibrating,
   said plates being shaped to affect the spectrum produced by said vibratory mechanism,
   the diameter of said mechanism being smaller than the skin fistula of the user.

9. The vibratory mechanism of claim 8 comprising
   a second reed attached to said first reed, said second reed being of smaller shape to said first reed,
   said first and second reed being attached to each other longitudinally so that the first reed is upstream and the second reed is downstream of the lung air during speech production.

* * * * *